(12) United States Patent
Kato

(10) Patent No.: US 7,553,444 B2
(45) Date of Patent: Jun. 30, 2009

(54) HEAT MOLD DEVICE AND A METHOD OF MAKING A GUIDE WIRE BY USING THE SAME HEAT MOLD DEVICE

(75) Inventor: Tomihisa Kato, Aichi-ken (JP)

(73) Assignee: Asahi Intecc Co., Ltd., Aichi-ken (JP)

( * ) Notice: Subject to any disclaimer, the term of this patent is extended or adjusted under 35 U.S.C. 154(b) by 314 days.

(21) Appl. No.: 11/443,487

(22) Filed: May 31, 2006

(65) Prior Publication Data

US 2006/0272751 A1 Dec. 7, 2006

(30) Foreign Application Priority Data

Jun. 6, 2005 (JP) ............................. 2005-166188

(51) Int. Cl.
*B21F 33/00* (2006.01)

(52) U.S. Cl. ...................... 266/249; 266/274; 29/33 F

(58) Field of Classification Search ....................... None
See application file for complete search history.

(56) References Cited

U.S. PATENT DOCUMENTS 3,586,303 A * 6/1971 Lee ............................ 266/274
5,409,558 A * 4/1995 Takahasi et al. .............. 156/172
6,271,601 B1 * 8/2001 Yamamoto et al. .......... 257/784
6,465,758 B1 10/2002 Ham

FOREIGN PATENT DOCUMENTS

| EP | 1 419 787 A1 | 5/2004 |
| JP | 7-255856 | 10/1995 |
| JP | 3300155 B | 4/2002 |
| JP | 2004-222880 | 8/2004 |

* cited by examiner

*Primary Examiner*—George Wyszomierski
(74) *Attorney, Agent, or Firm*—Morgan, Lewis & Bockius LLP

(57) ABSTRACT

In a heat mold device 1 for a guide wire 9, the metallic mold body 2 is made from the material, the thermal expansional coefficient of which is the same of a metallic coiled wire 91 to stabilize a shape-forming configuration 94. A plurality of the mold bodies 2 are arranged in a mold frame 6A to make the reverse side 22 of one mold body 2 tightly contact with the obverse side 21 of other mold body 2 among the neighboring mold bodies 2. A jig arm 7A sandwiches an array of metallic mold bodies 2 and the side plate 63 to serve as a securement member 7. Upon manufacturing the guide wire 9 well-suited to the medical field, the heat mold device 1 renders it possible to make a high quality guide wire with a high productivity.

13 Claims, 12 Drawing Sheets

HEAT MOLD DEVICE AND A METHOD OF MAKING A GUIDE WIRE BY USING THE SAME HEAT MOLD DEVICE

BACKGROUND OF THE INVENTION

1. Field of the Invention

The invention relates to a guide wire well-suited to the medical field upon assisting a catheter navigate into a vascular tracts, urethra, somatic organs or placing a retainer at an aneurysm-forming lesion in a vascular system, and particularly concerns to a heat mold device and a method of making the guide wire by using the heat mold device.

2. Description of Prior Art

Upon implementing a therapeutical treatment, prior to using a catheter, it is necessary to firstly insert a guide wire into a blood vessel as a guide for the catheter. In general, the flexible guide wire has a metallic coiled wire made by winding a stainless steel, platinum, gold or tungsten (wolfram) line around a mandrel. The guide wire has a core wire made by a stainless steel metal or a carbon steel metal, and having a safety wire to prevent the metallic coiled wire from inadvertently being stretched. A distal end portion of the metallic coiled wire is arcuated to define a shape-forming configuration.

Into the metallic coiled wire, the core wire and the safety wire are inserted. The safety wire has both end portions fixedly secured to the corresponding ends of the metallic coiled wire. The core wire is progressively reduced at its diameter as approaching its distal end to form a tapered configuration. The rear end of the core wire is fixed to a rear end of the metallic coiled wire. The core wire terminates its distal end portion short of the shape-forming configuration to render the configuration pliable so as not to get the blood vessel injured.

Upon making the guide wire to have the shape-forming configuration, Japanese Patent No. 3300155 introduces to insert a distal end portion of a guide wire into a mold groove provided with an outer surface of a metallic mold body. After putting the metallic mold body into a heating furnace with a lid placed on the metallic mold body, the distal end portion of the guide wire is thermally treated to form it arcuate as the shape-forming configuration.

However, it is not sufficient to only place the lid on the metallic mold body because the lid may be subjected to the thermal deformation due to the thermal expansional difference between the lid and the metallic mold body. This causes to fall the lid and the guide wire off the metallic mold body, thus making it not possible to render the shape-forming configuration into high quality product.

Due to the physical strains and deformations based on the thermal expansional difference between the lid and the metallic mold body, the guide wire is susceptible at its shape-forming configuration to the deformation especially when the guide wire is small in diameter (e.g., less than 1.0 mm in outer diameter). The Japanese Patent No. 3300155 remains silent about diversifying the shape-forming configuration, while at the same time, efficiently producing a plurality of guide wires concurrently with the common metallic mold body.

Therefore, the invention is made to eliminate the above drawbacks to provide a heat mold device which is capable of forming a guide wire arcuate as a shape-forming configuration, and preventing a lid body from inadvertently falling off, and diversifying the shape-forming configuration, while at the same time, efficiently producing a plurality of guide wires concurrently with the common metallic mold body.

It is also an object of the invention to provide a method of making a guide wire capable to produce high quality ones with a high efficiency.

SUMMARY OF THE INVENTION

According to the invention, there is provided a heat mold device, a tabulate mold body is provided, an outer surface of which has a mold groove. The mold groove forms an open-ended portion at an elevational side of the metallic mold body. A lid body is placed on the outer surface of the metallic mold body. The metallic mold body is made from the same sort of material which the metallic coiled wire is formed. The lid body has a lid plate to be in contact with the outer surface of the metallic mold body, and having a pushing member which is slidably fit into the metallic mold body to urgingly push the metallic mold body against the lid plate so as to hold the metallic mold body in place.

By forming the metallic mold body and the metallic coiled wire with the same sort of material (in terms of both thermal expansional coefficient and thermal conductivity), it is possible to stably form the shape-forming configuration due to no difference of the thermal expansional coefficient and thermal conductivity between the metallic mold body and the metallic coiled wire.

It is to be noted that the same sort of material means that the metallic mold body and the metallic coiled wire have the material identical in terms of both thermal expansional coefficient and thermal conductivity. It leads to the fact that the austenitic stainless steel and the austenitic free-cutting stainless steel has the same sort of material. This is because the main ingredients are common between the two steels, and the additives (lead, bismuth, etc.) of the austenitic free-cutting stainless steel are too small to differentiate the thermal expansional coefficient and the thermal conductivity between the two steels.

With the lid body having the lid plate which comes in contact with the obverse side of the metallic mold body, and the pushing member slidably fit into the metallic mold body, it is easy to attach the lid body to the metallic mold body.

By urgingly push the metallic mold body against the lid plate, it is possible to prevent the guide wire from inadvertently falling off the mold groove. It also prevents the hot air wind from directly blowing against the guide wire, thus substantially keeping the spatial temperature uniform between the lid body and the metallic mold body.

According to other aspect of the invention, a tabulate metallic mold body is provided, an obverse side of which has a mold groove. The mold groove forms an open-ended portion at an elevational side of the metallic mold body. A lid body is placed on the obverse side of the metallic mold body. The metallic mold body is made from the same sort of material which the metallic coiled wire is formed. A plurality of the metallic mold bodies are contiguously arranged to mutually overlap so as to make a reverse side of one metallic mold body tightly contact with the obverse side of other metallic mold body among the neighboring metallic mold bodies. A face plate is provided to engage with the obverse side of the metallic mold body positioned at one end side among the plurality of the metallic mold bodies. A securement member is provided to fixedly secure the face plate to the metallic mold body.

Such is the structure that the plurality of the metallic mold bodies are contiguously arranged to make a reverse side of one metallic mold body tightly contact with the obverse side of other metallic mold body among the neighboring metallic mold bodies. The structure makes it possible to make the one metallic mold body serve as a lid member for the other metallic mold body. The face plate engages with the obverse side of the metallic mold body positioned at one end side among the plurality of the metallic mold bodies. This means that the face plate serves as a lid member, thus eliminating the need of placing the lid member on each of the metallic mold bodies so as to advantageously reduce the number of assembling procedures.

With the face plate and the metallic mold bodies fixed by the securement member, it is possible to prevent the metallic coiled wire from inadvertently falling off the metallic mold body.

By arranging the plurality of the metallic mold bodies to mutually overlap, it is possible to dispense with less space in the furnace so as to attain a space-saving advantage, as opposed to the case in which the metallic mold bodies are individually placed in the furnace.

According to other aspect of the invention, the mold groove has a linear straight portion which branches into two or more arcuated portions. This makes it possible to form two or more shape-forming configurations with the common metallic mold body.

This eliminates the need of replacing the metallic mold bodies each time when exchanging the shape-forming configurations, thus making it possible to advantageously reduce the number of assembling procedures.

According to other aspect of the invention, the mold groove has an open-ended portion at both elevational sides of the metallic mold body, and the mold groove extends from the open-ended portion along a path corresponding to the shape-forming configuration.

This makes it possible to insert the metallic coiled wire into any one of the elevational sides of the metallic mold body without changing the setting directions of the metallic mold body. This contributes to efficiently assembling the metallic coiled wire to the metallic mold body, thereby attaining the space-saving advantage in the working area upon assembling the metallic coiled wire.

According to other aspect of the invention, the mold groove is defined on both the obverse and reverse sides of the mold body. This makes it possible to provide the shape-forming configuration on two guide wires concurrently, thus enabling manufacturers to improve the productivity.

According to other aspect of the invention, a plurality of the mold grooves are aligned in parallel with each other. This makes it possible to provide the shape-forming configuration on the plurality of guide wires concurrently, thus enabling manufacturers to significantly improve the productivity.

According to other aspect of the invention, the pushing member has a side plate extended from both sides of the lid plate in the reverse direction of the metallic mold body and further having an end plate extended from both the sides of the lid plate so as to urgingly engage with the reverse side of the metallic mold body.

Such is the structure that the pushing member pushes the metallic mold body against the lid plate to hold the metallic mold body in place, thus preventing the lid body and the guide wire in the mold groove from inadvertently falling off the metallic mold body.

According to other aspect of the invention, the pushing member has a protrusion directed toward the obverse side of the metallic mold body.

With the pushing member pushing the metallic mold body against the lid plate to positively hold the metallic mold body in place, thus preventing the lid body and the guide wire in the mold groove from inadvertently falling off the metallic mold body.

According to other aspect of the invention, the pushing member bends the lid body into a curved configuration with the end plate set inside the lid plate.

With the pushing member positively pushing the metallic mold body against the lid plate to stably hold the metallic mold body in place, thus preventing the lid body and the guide wire in the mold groove from inadvertently falling off the metallic mold body.

According to other aspect of the invention, the lid plate has a protrusion directed opposite to the end plate.

This makes it possible to resist the permanent set in fatigue caused by detachably mounting the lid body against the metallic mold body even under the cyclic environment of the high temperature and the normal temperature.

According to other aspect of the invention, each of the metallic mold bodies has a ventilation hole. With the ventilation hole provided on the metallic mold bodies, it is possible to give uniform amount of heat to each of the metallic mold bodies even when a plurality of the metallic mold bodies are contiguously arranged to mutually overlap so as to make the reverse side of one metallic mold body tightly contact with the obverse side of other metallic mold body.

According to other aspect of the invention, the securement member has a jig arm to fixedly sandwich the metallic mold body and the face plate together. The jig arm has a predetermined length corresponding to a total thickness of each of the metallic mold bodies and the face plate including a total number of the metallic mold bodies.

With the use of the jig arm, it is possible to fixedly unite the metallic mold body and the face plate together without using a special tool.

With the jig arm having the length corresponding to a total thickness of each of the metallic mold bodies and the face plate, it is possible to set a predetermined number of the metallic mold bodies. By knowing how many metallic coiled wires one unit of the metallic mold body has, it becomes possible to calculate how many guide wires will be produced in total without counting the number of the metallic mold bodies.

According to other aspect of the invention, provided is a method of making a guide wire by using the heat mold device thus far described. It is possible to produce a high quality guide wire with a high efficiency.

According to other aspect of the invention, the metallic coiled wire is formed by a magnetized austenitic stainless steel wire. This makes it possible to readily attach the metallic coiled wire to the metallic mold body. By setting a magnet on the reverse side of the metallic mold body, the magnet adheres the metallic coiled wire to the metallic mold body so as to make the assembling procedures smooth and easy.

With the austenitic stainless steel wire represents substantially no quench-hardening and hot-short property, it is possible to maintain the guide wire flexible after thermally treating the guide wire.

According to other aspect of the invention, a safety wire is inserted into the metallic coiled wire. A front end of the safety wire is fixedly secured to one end of the metallic coiled wire which is to be shaped as a shape-forming configuration, while at the same time, freely setting the other portion than secured to the metallic coiled wire with the other portion extended outside the metallic coiled wire. The metallic coiled wire is shaped within the metallic mold body by means of a thermal treatment. Thereafter, the safety wire is severed at its portion extended outside the metallic coiled wire. The severed portion is fixedly secured to the other end of the metallic coiled wire.

Since the bending action causes the metallic coiled wire to induce coil line gaps at the side which represents a larger radius of curvature, the safety wire is subjected to a tensile stress when both ends of the safety wire are fixed to the respective ends of the metallic coiled wire. This is because the bending action permits the metallic coiled wire to expand, while remaining the safety wire unstretched. As a result, the bending action may snap the safety wire with the increase of the tensile stress.

By fixedly securing only the front end portion with other portion set free, it is possible to make the safety wire immune to the tensile stress so as to protect it against the breakage upon providing the shape-forming configuration on the metallic coiled wire.

According to other aspect of the invention, the metallic coiled wire is shaped within the metallic mold body by means of the thermal treatment. Thereafter, the safety wire and a core wire are inserted into the metallic coiled wire, and a front end of the safety wire is fixedly secured to one end of the metallic coiled wire which is to be shaped as the shaped-formed configuration. Each rear end of the safety wire and the core wire is fixedly secured to the other end of the metallic coiled wire.

With the safety wire and the core wire inserted into the metallic coiled wire after the metallic coiled wire is thermally treated, it is possible to mitigate the tensile stress, to which the safety wire is subjected.

This makes it possible to reduce the fear that the safety wire may be snapped due to the tensile stress which would occur on the safety wire when the safety wire and the core wire are inserted into the metallic coiled wire prior to conducting the thermal treatment, and both the ends of the safety wire are fixed to the respective ends of the metallic coiled wire.

According to other aspect of the invention, an outer surface of the guide wire is treated with an electrolytic polishing after treating it with the thermal treatment or a ultrasonic cleaning after treating it with the electrolytic polishing. This makes it possible to impart a corrosion-resistant property to the guide wire.

According to other aspect of the invention, an outer surface of the metallic coiled wire is coated with a synthetic layer, and an outer surface of the synthetic layer is further coated with a hydrophilic polymer layer. This makes it possible to impart a lubricity to the outer surface of the guide wire.

BRIEF DESCRIPTION OF THE DRAWINGS

Preferred forms of the present invention are illustrated in the accompanying drawings in which.

DETAILED DESCRIPTION OF THE PREFERRED EMBODIMENTS

Figure 1:
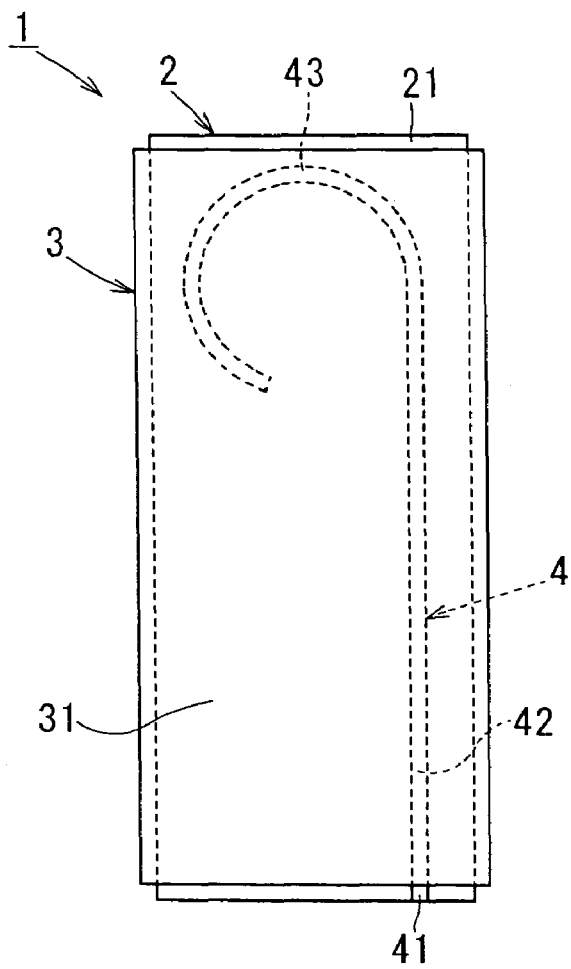
FIG. 1 is a plan view of a heat mold device according to a first embodiment of the invention.
Figure 2:
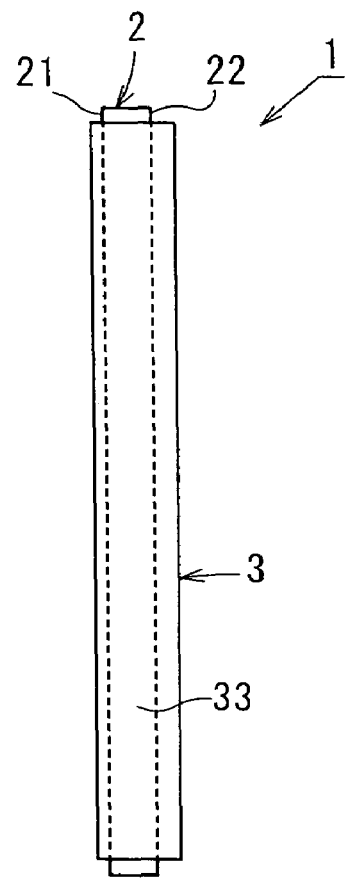
FIG. 2 is a bottom side view of the heat mold device.
Figure 3:
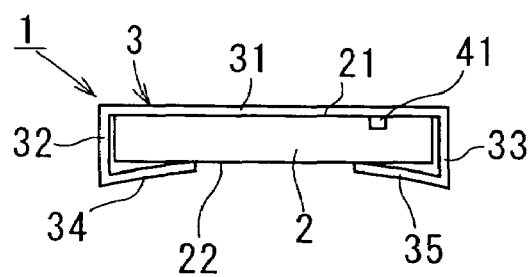
FIG. 3 is an elevational side view of the heat mold device.

In the following description of the depicted embodiments, the same reference numerals are used for features of the same type.

First Embodiment

Referring to FIGS. 1 through 4 and 12 which show a heat mold device 1 according to a first embodiment of the invention, the heat mold device 1 has a tabulate mold body 2 (referred to only as "mold body 2" hereinafter) and a lid body 3 which is to be placed on the mold body 2.

The mold body 2 is made from the same sort of material as a metallic coiled wire 91 of a guide wire 9 is made. Namely, the metallic coiled wire 91 is made from an austenitic stainless steel line. The mold body 2 is made from an austenitic stainless steel or an austenitic free-cutting stainless steel, both of which have a common thermal expansional coefficient and thermal conductivity. The mold body 2 is rectangular in shape with long sides extending along the lengthwise direction and short sides along the crosswise direction. On an outer surface 21 of the mold body 2, provided is a mold groove 4 along the lengthwise direction.

The mold groove 4 has an open-ended portion 41 at the short sides along the crosswise direction. A linear straight portion 42 of the mold groove 4 extends from the open-ended portion 41 and continuously branches into an arcuate portion 43 (approx. 270 degrees in circumferential angle). The mold groove 4 is rectangular in cross section, and has a depth (e.g., 0.9 mm (0.0354 inch)) and width (e.g., 0.9 mm (0.0354 inch)) each corresponding to the diametrical size (e.g., 0.89 mm (0.0350 inch)) of the guide wire 9. The cross section of the mold groove 4 may be semi-circular, V-shaped or oval instead of the rectangle.

The lid body 3 is made from a metallic material, preferably the same material as the mold body 2 is made. The lid body 3 has a lid plate 31 which comes in contact with the outer surface of the mold body 2, and further having a pushing member (end plates 34, 35) which slidably fits into the mold body 2 to urgingly push the mold body 2 against the lid plate 31 so as to hold the mold body 2 in place. The lid body 3 is formed by bending a sheet of rectangular metal, and having the lid plate 31 which covers the outer surface 21 of the mold body 2. The lid body 3 further has side plates 32, 33 each provided to cover lengthwise sides of the mold body 2. The lid body 3 urgingly engage the end plates 34, 35 against a reverse side of the mold body 2 to serve as the pushing member.

The lid plate 31 is somewhat shorter in the lengthwise direction than the mold body 2, but slightly longer in the crosswise direction than the mold body 2. The lid plate 31 is shorter in the lengthwise direction because the shorter side length makes a mounting-and-demounting operation easy upon attaching and withdrawing the lid body 3 against the mold body 2.

The lid plate 31 has the side plates 32, 33 turned by approx. 90 degrees toward the reverse direction of the mold body 2. The side plates 32, 33 have a height somewhat greater than a thickness of the mold body 2. The side plates 32, 33 have end plates 34, 35 turned inward by approx. 130 degrees, so that a front end of the end plates 34, 35 urgingly engages with the reverse side 22 of the mold body 2. The side plates 32, 33 and the end plates 34, 35 work to slidably hold the lid body 3 in the lengthwise direction against the mold body 2.

Method of the First Embodiment

Figure 22:
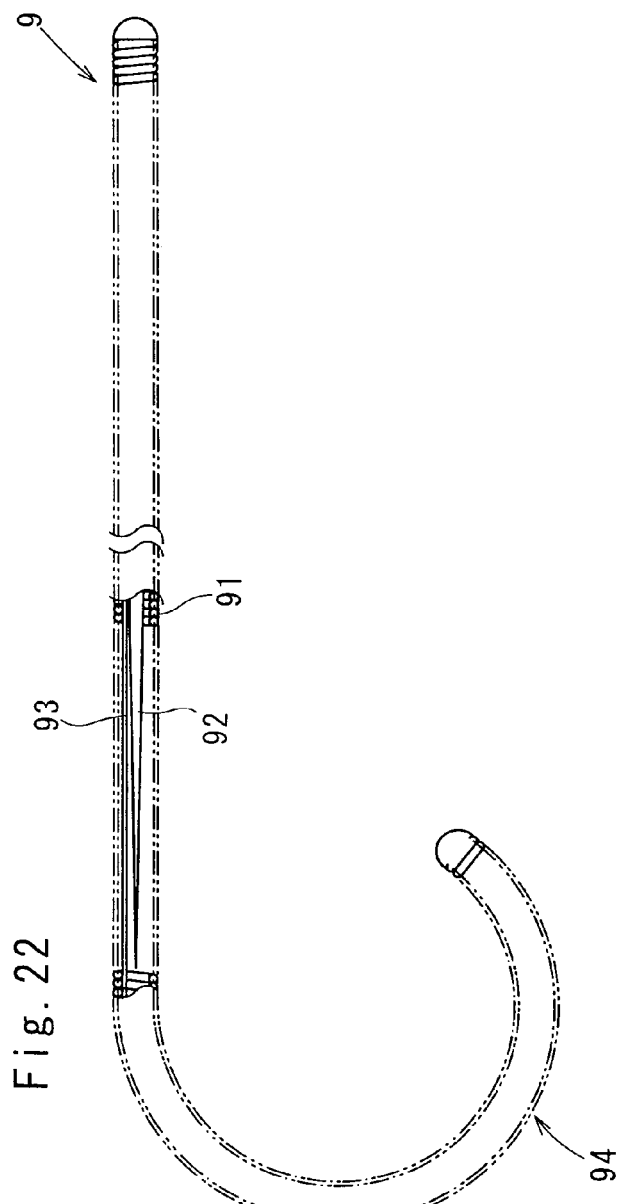
FIG. 22 is a plan view of the guide wire, but partly sectioned.
Figure 24:
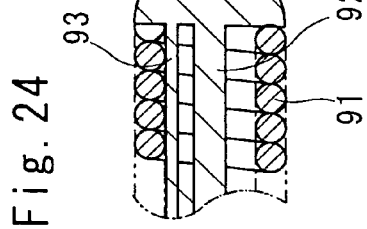
FIG. 24 is an enlarged cross sectional view of a proximal end of the guide wire.
Figure 23:
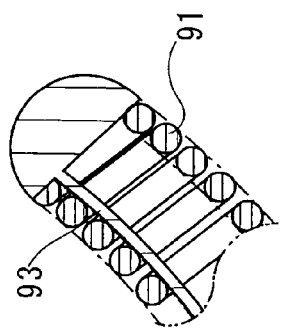
FIG. 23 is an enlarged cross sectional view of a distal end of the guide wire.

As shown in FIG. 22, the guide wire 9 has the metallic coiled wire 91 into which a core wire 92 and a safety wire 93 are inserted. The safety wire 93 is fixed at both ends to the respective ends of the metallic coiled wire 91 as shown in FIGS. 23, 24. The core wire 92 has a tapered portion at the distal end section, and having a proximal end fixed to the proximal end of the metallic coiled wire 91. A distal end portion of the guide wire 9 is arcuately bent to serve as a shape-forming configuration 94. The guide wire 9 thus described is manufactured as follows:

With the safety wire 93 inserted into the metallic coiled wire 91, the distal end of the safety wire 93 is fixedly secured to the distal end of the metallic coiled wire 91 by means of a soldering procedure. The distal end of the metallic coiled wire 91 is to be bend as the shape-forming configuration 94.

The proximal end of the safety wire 93 passes freely through an inner space of the metallic coiled wire 91 to extend outside the metallic coiled wire 91.

Figure 4:
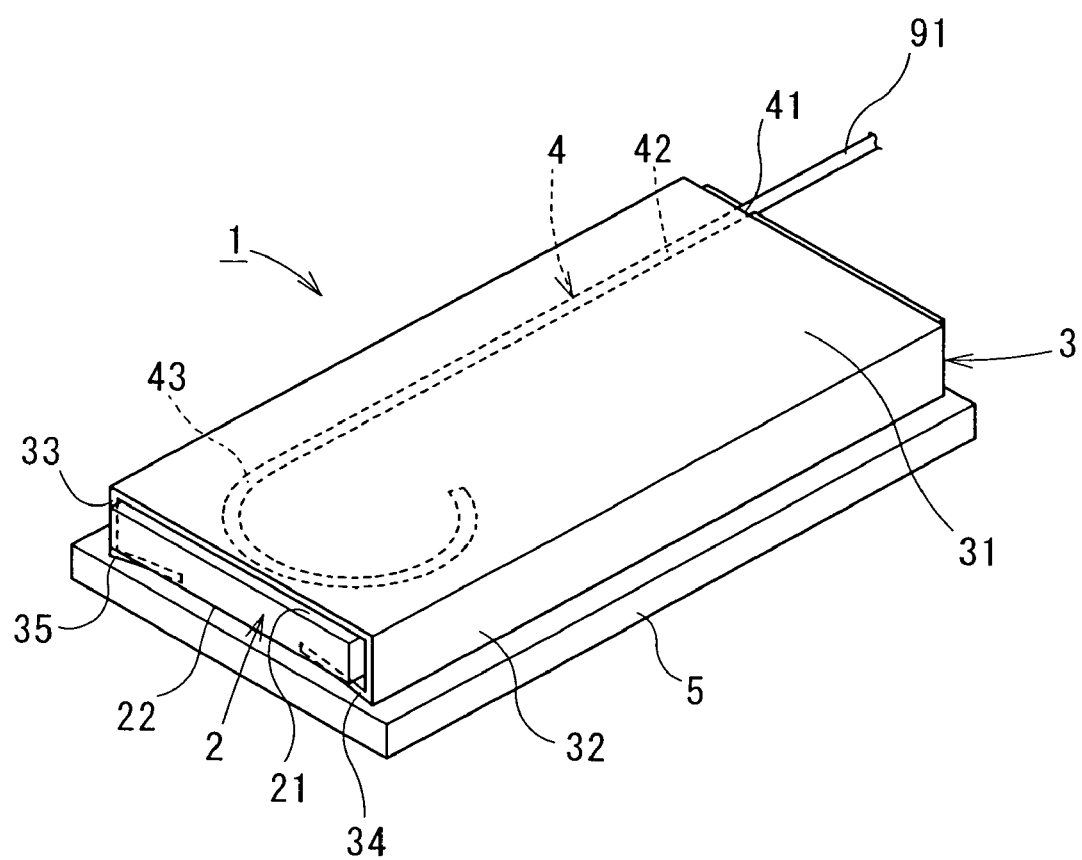
FIG. 4 is a perspective view of the heat mold device, to which a metallic coiled wire is attached.

With a magnetized pedestal 5 placed on an underside of the mold body 2, the distal end of the metallic coiled wire 91 is placed into the mold groove 4 before assembling the lid body 3 to the mold body 2 as shown in FIG. 4. After removing the magnetized pedestal 5, the heat mold device 1 is placed in a heating furnace (not shown) to thermally treat the distal end of the metallic coiled wire 91 held by the mold body 2.

After shaping the distal end of the metallic coiled wire 91 with the thermal treatment, the core wire 92 is inserted into the metallic coiled wire 91. The core wire 92 and the safety wire 93 are severed at the lengthwise portion which extends outside the metallic coiled wire 91. The severed ends of the core wired 92 and the safety wire 91 are each fixedly secured to the proximal end of the metallic coiled wire 91.

Then, the arcuate portion served as the shape-forming configuration 94 is dipped into electrolyte solution before electrolytically polished by means of a well-known procedure. The polished surface is treated with the ultrasonic cleaning depending on the necessity.

With the use of a spray gun (not shown), polytetrafluoroethylene (PTFE) is coated on the outer surface of the guide wire 9 with the guide wire 9 attached to a suspension jig (not shown). Then, the guide wire 9 is placed in the furnace at 380° C. for 30 minutes so as to provide a synthetic layer on the outer surface of the guide wire 9. By means of the dipping procedure, a hydrophilic polymer is coated on an outer surface of the synthetic layer.

Advantages of the First Embodiment

With the mold body 2 made by the same material of the metallic coiled wire 91, it is possible to eliminate the difference between the mold body 2 and the metallic coiled wire 9 in terms of the thermal expansional coefficient and thermal conductivity. This stabilizes the shape-forming configuration 94 provided on the distal end portion of the metallic coiled wire 91.

The metallic coiled wire 91 is made of the austenitic stainless steel which has the thermal expansional coefficient 1.5-1.6 times greater than the general carbon steel. When the mold body 2 is made of the general carbon steel, the metallic coiled wire 91 in the mold groove 4 is likely subjected to meander, strains and deformation due to the thermal expansional difference between the mold body 2 and the metallic coiled wire 91, and thus making it difficult to easily take the metallic coiled wire 91 out of the mold groove 4.

With a time lag occurred in temperature rise between the mold body 2 and the metallic coiled wire 91, the metallic coiled wire 91 in the mold groove 4 is also likely subjected to the serpentine deformation due to the strains.

This is all the more true especially when using the guide wire 9 (0.89 mm in dia.) and the safety wire 93 (0.265 mm in width and 0.065 mm in thickness) because they are susceptible to the thermal influence.

On the contrary, with the use of the austenitic stainless steel or the austenitic free-cutting stainless steel for the mold body 2 and the metallic coiled wire 91, it is possible to remove the above drawbacks so as to advantageously stabilize the shape-forming configuration 94 defined on the distal end portion of the metallic coiled wire 9. It is to be noted that the reason why the austenitic free-cutting stainless steel is applied to the mold body 2 is the necessity of defining the extremely narrow mold groove 4 (0.9 mm (0.0354 inch) in depth and width) on its outer surface 21 in the arcuate configuration 94.

The austenitic free-cutting stainless steel imparts a long life span to the mold body 2 and makes the disposal of the cutting chips easy. It is also preferable to adopt the austenitic free-cutting stainless steel from the point of maintaining the outer surface 21 smooth and protecting the mold groove 4 against injuries.

With the end plates 34, 35 urgingly engaged their front ends with the reverse surface 22 of the mold body 2, it is possible to hold the lid body 3 and the metallic coiled wire 91 in place and prevent them from inadvertently falling off. With the lid body 3 provided to cover the outer surface 21 of the mold body 2, it is possible to prevent the hot air wind from directly blowing against the guide wire 9 in the mold groove 4. This makes it possible to uniformly maintain the spatial temperature between the lid body 3 and the mold body 2.

The metallic coiled wire 91 is made from the austenitic stainless steel line in the present method of making the guide wire 9. The wire-drawing procedure magnetizes the austenitic stainless steel line due to the work-induced metamorphosis. Upon placing the metallic coiled wire 91 on the mold groove 4, the metallic coiled wire 91 has a tendency to be attracted inward the mold groove 4 against the magnetized pedestal 5. This makes it easy to assemble the metallic coiled wire 91 to the mold groove 4. With the use of the austenitic stainless steel line, it is possible to maintain the guide wire 9 flexible due to the absence of the quench-hardening and hot-short properties.

In the method of making the guide wire, the safety wire 93 is inserted into the metallic coiled wire 91. A front end of the safety wire 93 is fixedly secured to one end of the metallic coiled wire 91 which is to be shaped as the shape-forming configuration 94, while at the same time, freely setting the other portion than secured to the metallic coiled wire 91 with the other portion extended outside the metallic coiled wire 91. The metallic coiled wire 91 is shaped within the mold body 2 by means of the thermal treatment.

Since the bending action causes the metallic coiled wire 91 to induce coil line gaps at the side which represents a larger radius of curvature, the safety wire 93 is subjected to a tensile stress when both ends of the safety wire 93 are fixed to the respective ends of the metallic coiled wire 91. This is because the bending action permits the metallic coiled wire 91 to expand, while remaining the safety wire 93 unstretched. As a result, the bending action may snap the safety wire 93 with the increase of the tensile stress.

By fixedly securing only the front end portion with other portion set free, it is possibile to make the safety wire 93 substantially immune to the tensile stress so as to protect it against the breakage upon providing the shape-forming configuration 94 on the metallic coiled wire 91.

Upon applying the austenitic stainless steel line to the metallic coiled wire 91, the cold wire-drawing procedure magnetizes the metallic coiled wire 91 due to the work-induced metamophorsis and represents a mirror-finished surface by means of an ironing dice. This causes the intermolecular van del Waals' force to appear on the outer surface of the metallic coiled wire 91 so as to attract foreign matters (e.g., minute ferrous particulates) even from the reason that the metallic coiled wire 91 has the coiled line structure. This induces the clearance corrosion and the particulate-related rust on the metallic coiled wire 91 so as to reduce the corrosion-resistant property.

By dipping the guide wire 9 into the electrolytic solution to treat with the electrolytic polishing and the ultrasonic cleaning after providing the shape-forming configuration 94, it is possible to remove the oxidized scales from the outer surface of the guide wire 9 to recover its inherent chromium component, thus causing to coat an inactive film to resultantly improve the corrosion-resistant property.

After thermally treating the guide wire 9, the synthetic layer is coated on the outer surface of the guide wire 9, and the hydrophilic polymer layer is coated on the outer surface of the synthetic layer. This makes it possible to smoothly insert the guide wire 9 into the blood vessel, urethra, bronchia or the like. It is to be noted that the hydrophilic polymer layer introduced herein means the lubricant (e.g., polyvinylpyrrolidone) which shows the lubricity when moistened.

Figure 5:
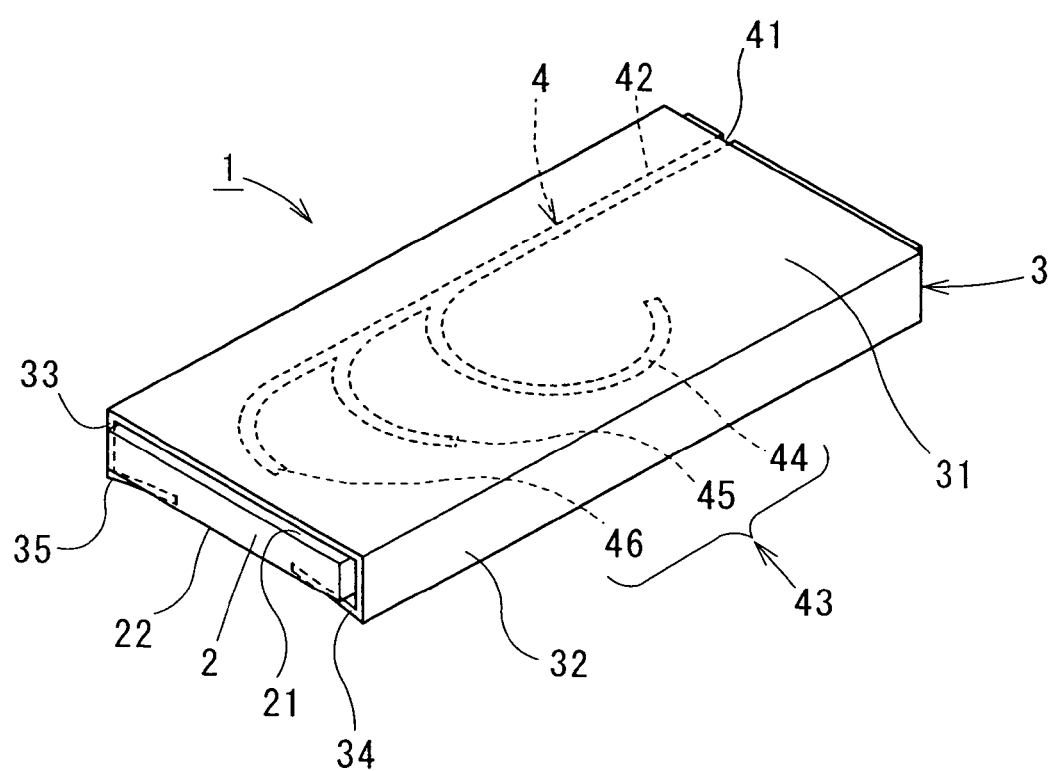
FIGS. 5-8 are perspective views of the heat mold device represented from a second embodiment to a fifth embodiment of the invention.

FIG. 5 show a second embodiment of the invention in which the heat mold device 1 has the mold groove 4 extending along the outer surface 21 from an open-ended portion 41 at the short side in parallel with the crosswise direction of the mold body 2. The mold groove 4 has a linear straight portion 42 which branches into three types of arcuate portions 43 (44-46). The arcuate portions 43 has a first bend section 44 (smaller radius of curvature), a second bend section 45 (medium radius of curvature) and a third bend section 46 (larger radius of curvature).

Method of the Second Embodiment

The method of making the guide wire 9 is in the following procedures.

The distal end portion of the metallic coiled wire 91 is selectively inserted into one of the arcuate portions 43 (44-46) of the mold body 2. Then, the lid body 3 is placed on the mold body 2 to cover the distal end portion of the metallic coiled wire 91. The heat mold device 1 is placed in the furnace with the metallic coiled wire 91 assembled between the lid body 3 and the mold body 2 so as to thermally treat the distal end portion of the metallic coiled wire 91 (shape-forming thermal treatment).

After the end of the thermal treatment, the core wire 92 and the safety wire 93 are inserted into the metallic coiled wire 91 to thermally weld the distal end of the safety wire 93 to the distal end of the metallic coiled wire 91. The proximal ends of the core wire 92 and the safety wire 93 are thermally welded to the respective proximal end of the metallic coiled wire 91.

Advantages of the Second Embodiment

The mold body 2 has the three types of arcuate portions 43 branched into the first bend section 44, the second bend section 45 and the third bend section 46. This enables the manufacturer to shape the distal end portion of the metallic coiled wire 91 into three types of configurations with the use of the common mold body 2.

This eliminates the necessity of exchanging the mold bodies each time when differently shaping the distal end portion of the metallic coiled wire 91, thus reducing the number of assembling procedures to improve the productivity.

With the safety wire 93 and the core wire 92 inserted into the metallic coiled wire 91 to thermally weld the formers to the latter after the metallic coiled wire 91 is thermally treated, it is possible to mitigate the tensile stress, to which the safety wire 93 is subjected.

This makes it possible to reduce the fear that the safety wire 93 may be snapped due to the tensile stress which would occur on the safety wire 93 when the safety wire 93 and the core wire 92 are inserted into the metallic coiled wire 91 prior to conducting the thermal treatment, and both the ends of the safety wire 93 are fixed to the respective ends of the metallic coiled wire 91.

Third Embodiment

Figure 6:
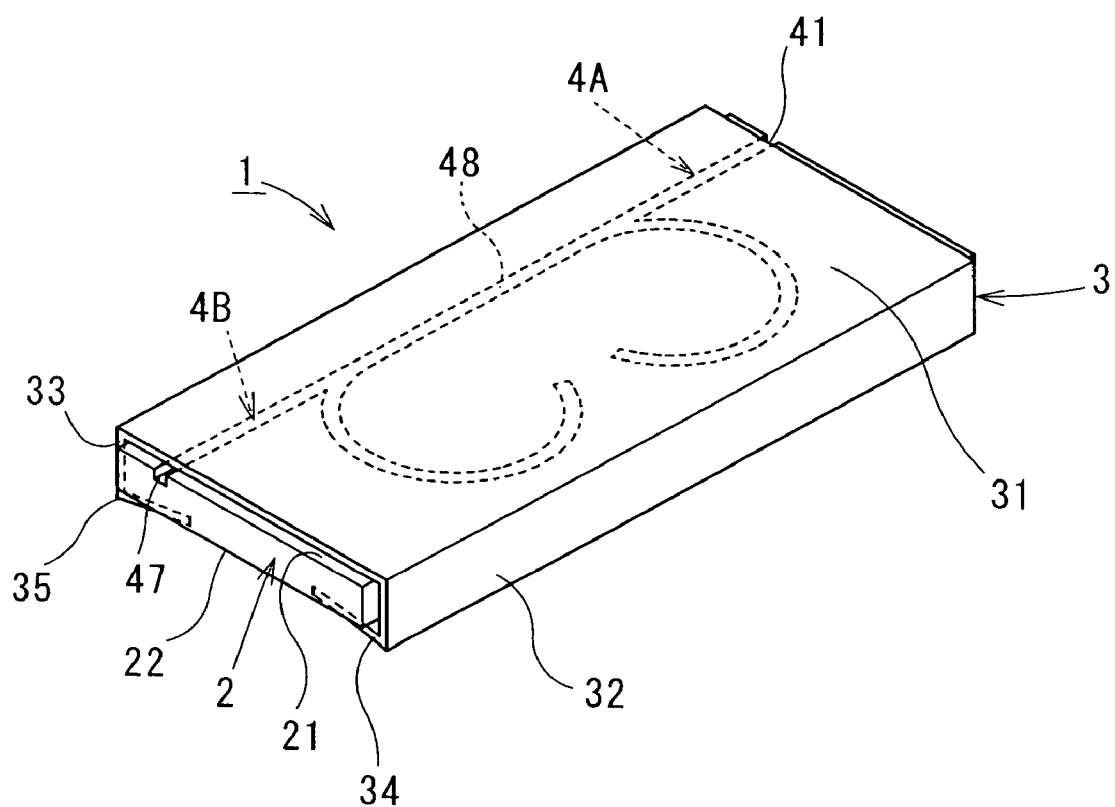

FIG. 6 shows a third embodiment of the invention in which a first mold groove 4A is provided on the outer surface of the mold body 2 to have the open-ended portion 41 at the side in parallel with the short side of the mold body 2. A second mold groove 4B is provided with the outer surface 21 of the mold body 2 to have an open-ended portion 47 in the opposite side of the open-ended portion 41. The second mold groove 4B is in a symmetrical relationship with the first mold groove 4A to have a common linear portion 48 along the same line. It is to be noted that the second mold groove 4B may be on the uneven and different line with the first mold groove 4A.

With the first mold groove 4A and the second mold groove 4B provided on the outer surface 21 of the mold body 2, it is possible to insert the metallic coiled wire 91 into any one of the elevational sides (open-ended portions 41, 47) of the mold body 2 without changing the setting directions of the mold body 2. This contributes to efficiently assembling the metallic coiled wire 91 to the mold body 2, thereby attaining the space-saving advantage in the working area upon assembling the metallic coiled wire 91.

Fourth Embodiment

Figure 7:
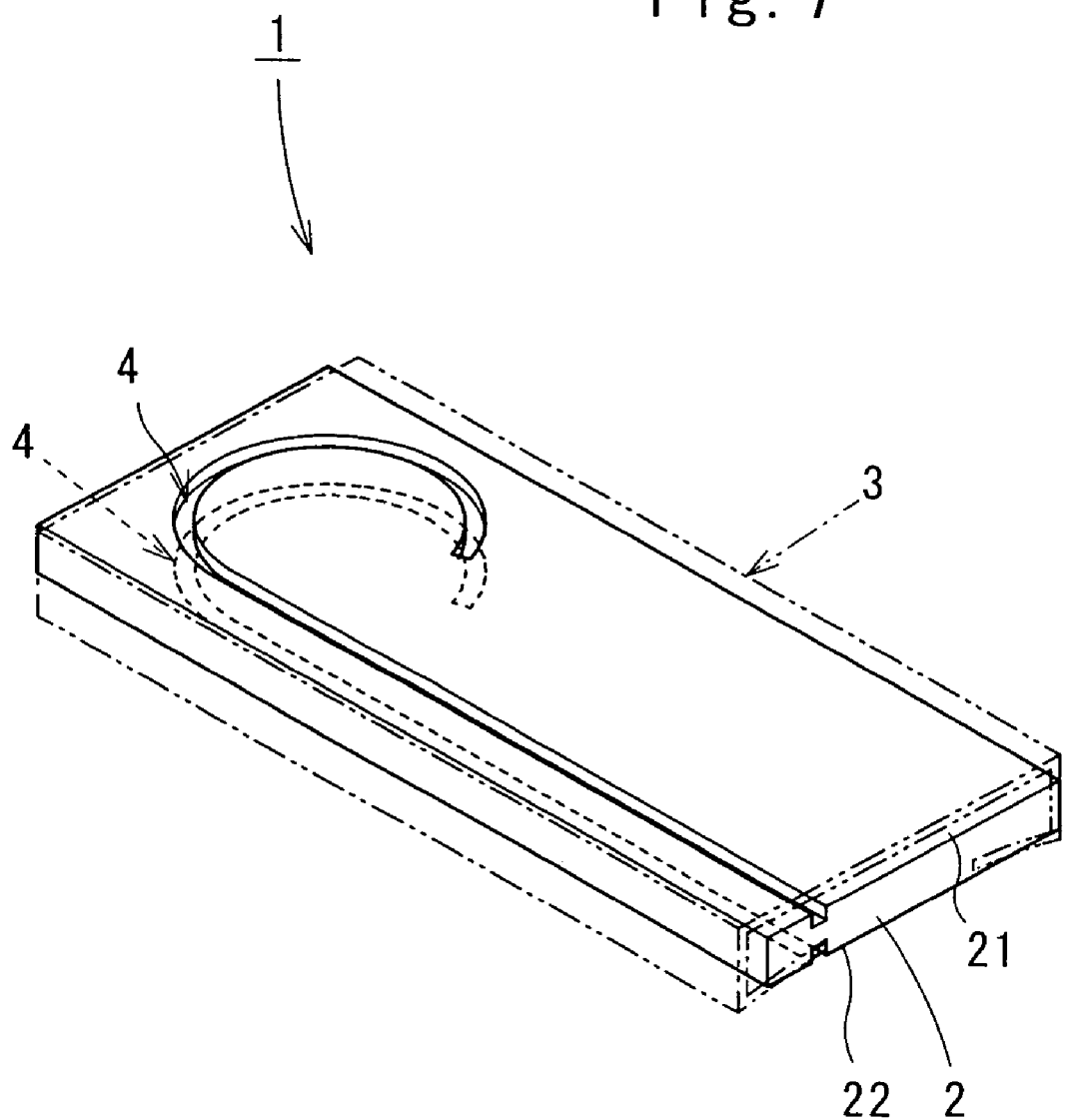

FIG. 7 shows a fourth embodiment of the invention in which the mold body 2 has the mold groove 4 on both the reverse side and the obverse side of the mold body 2. The two mold grooves 4 may be differently formed instead of shaping them identically. With the two mold grooves 4 provided on the mold body 2, it is possible to concurrently make two guide wires so as to improve the productivity.

Fifth Embodiment

Figure 8:
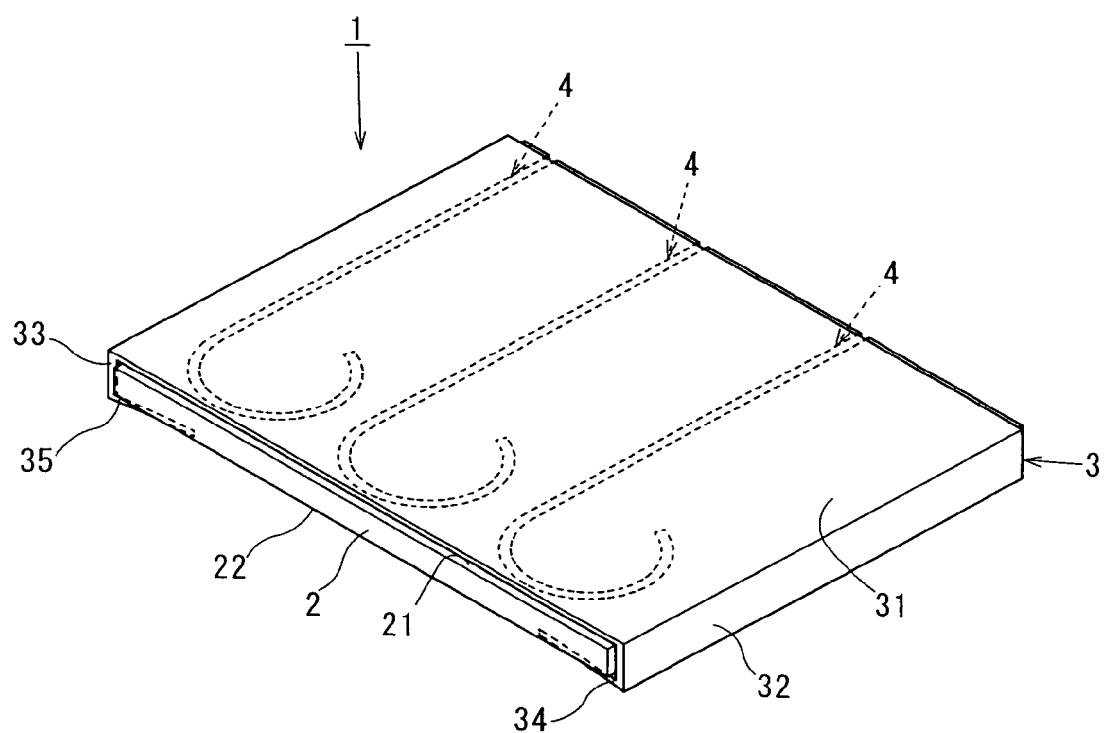

FIG. 8 shows a fifth embodiment of the invention in which a plurality of mold grooves 4 are provided on the mold body 2 aligned in parallel with each other. This makes it possible to produce a plural number of guide wires (e.g., three pieces) concurrently with the single common mold body 2 so as to improve the productivity.

Sixth Embodiment

Figure 9:
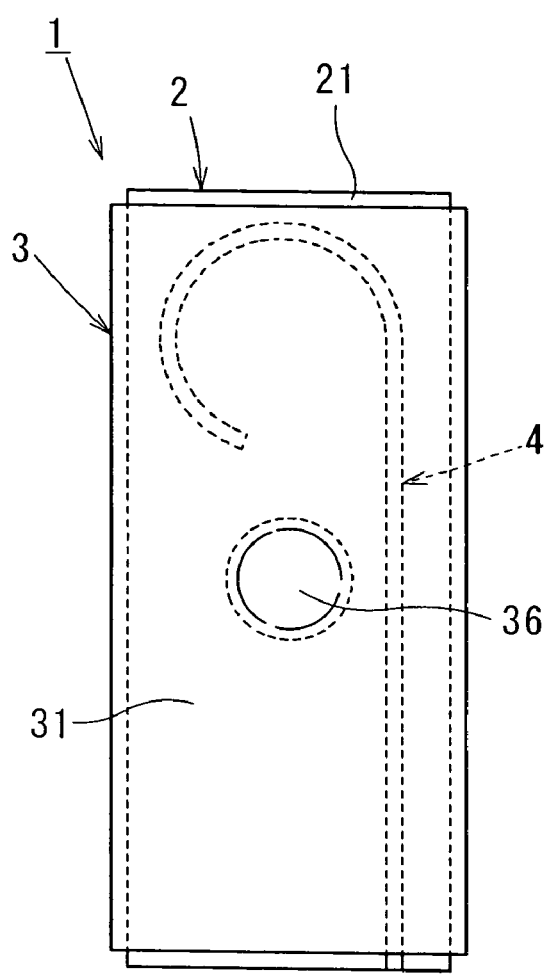
FIG. 9 is a plan view of a heat mold device according to a sixth embodiment of the invention.
Figure 10:
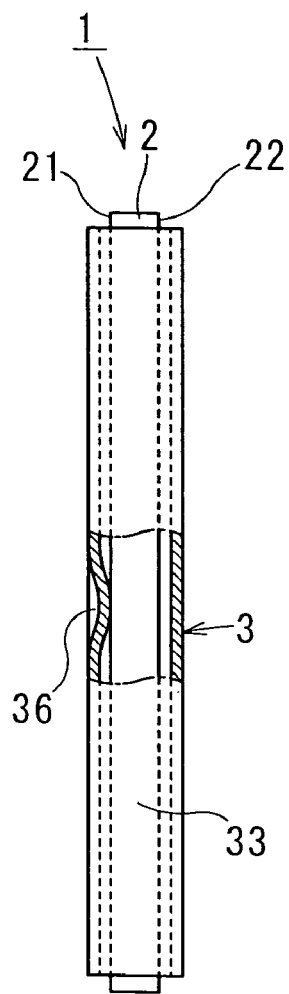
FIG. 10 is a bottom side view of the heat mold device.
Figure 11:
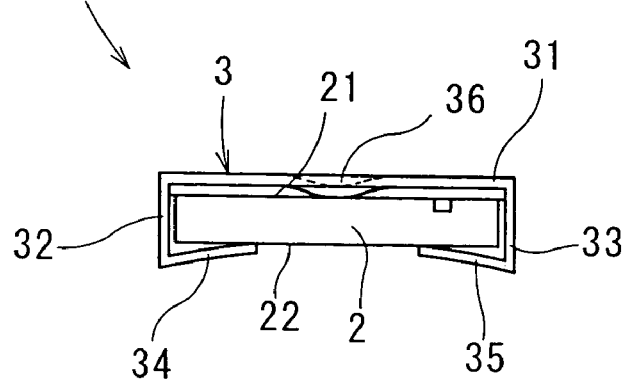
FIG. 11 is an elevational side view of the heat mold device.

FIGS. 9 through 11 show a sixth embodiment of the invention in which the lid plate 31 has a protrusion directed toward the outer surface 21 of the mold body 2. Namely, a central portion of the lid plate 31 is depressed to form a dent 36 which is to engage with outer surface 21 of the mold body 2 when the lid body 3 is assembled to the mold body 2.

With the protrusion defined on the lid plate 31 in addition to the end plates 34, 35, it is possible to increase the force pushed against the mold body 2 to positively hold the mold body 2 in place. This positively avoids the lid body 3 and the metallic coiled wire 91 from inadvertently falling off. It is to be noted that instead of providing the protrusion on the lid plate 31, the protrusion may be provided on the outer surface 21 of the mold body 2 so as to make the protrusion engage with the reverse side of the lid plate 31.

Seventh Embodiment

Figure 12:
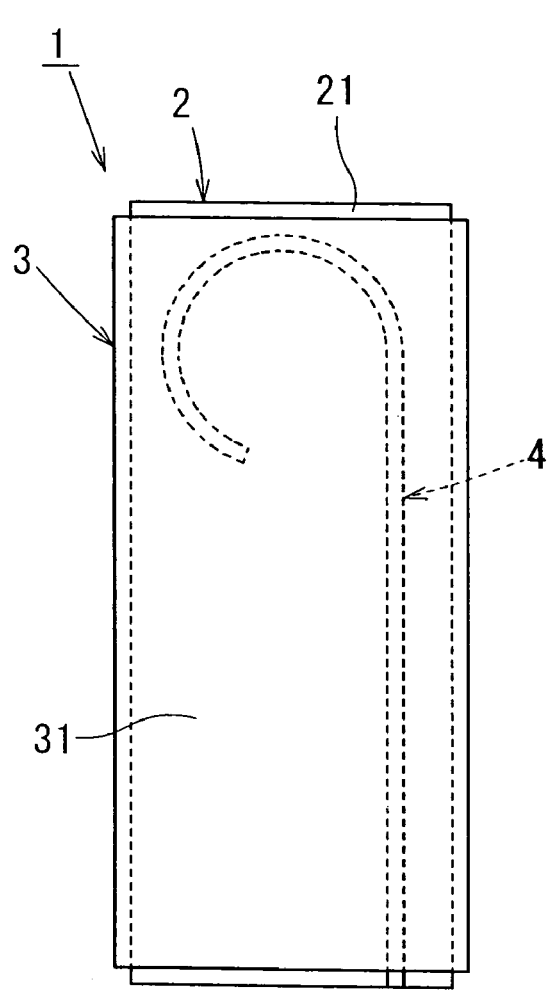
FIG. 12 is a plan view of a heat mold device according to a seventh embodiment of the invention.
Figure 13:
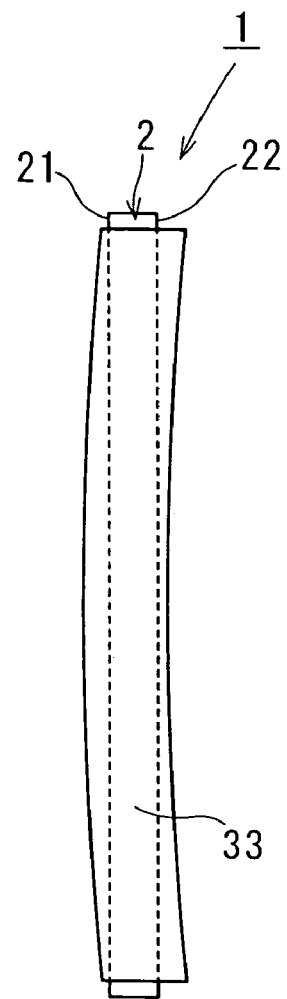
FIG. 13 is a bottom side view of the heat mold device.
Figure 14:
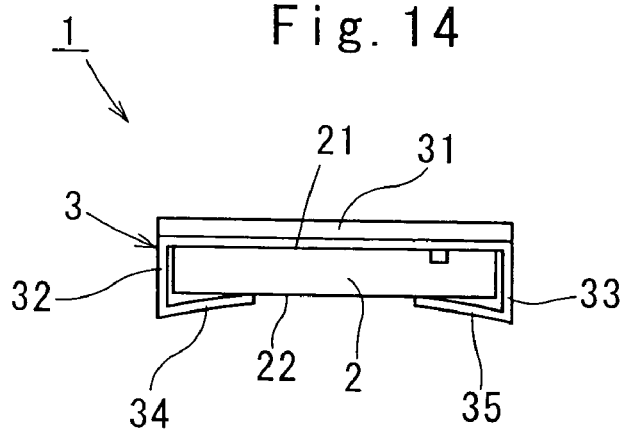
FIG. 14 is an elevational side view of the heat mold device.

FIGS. 12 through 14 show a seventh embodiment of the invention in which the lid body 3 is curved along the lengthwise direction with the end plates 34, 35 directed inward.

The curved lid body 3 makes it possible to increase the force pushing against the mold body 2 due to an elastic counterforce so as to more tightly hold the mold body 2 within the lid body 3 upon assembling the lid body 3 to the mold body 2. This is true when the heat mold device 1 is placed in the furnace. This also positively avoids the lid body 3 and the metallic coiled wire 91 from inadvertently falling off. It is to be noted that the lid body 3 may be curved along the crosswise direction.

Eighth Embodiment

Figure 15:
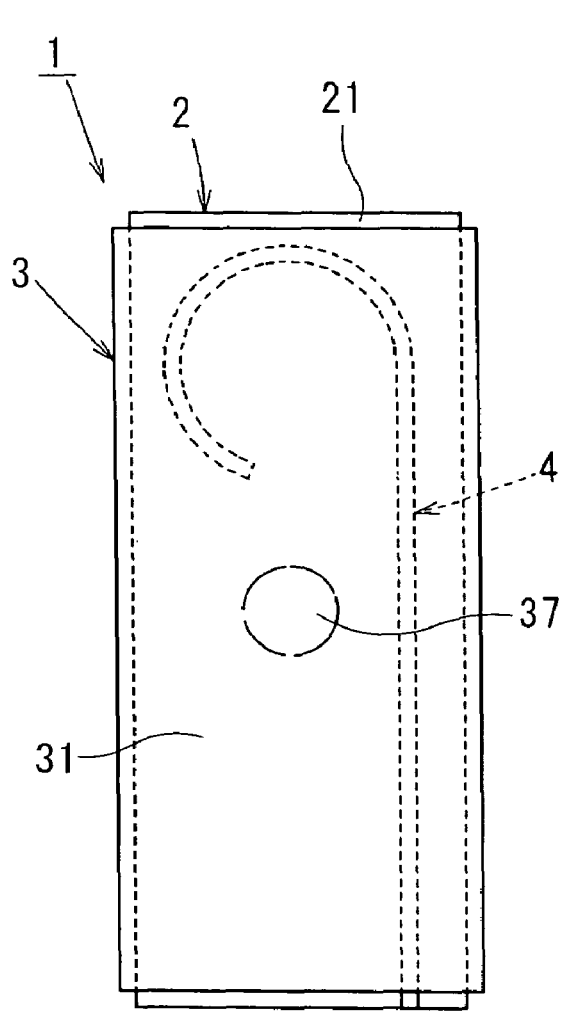
FIG. 15 is a plan view of a heat mold device according to an eighth embodiment of the invention.
Figure 16:
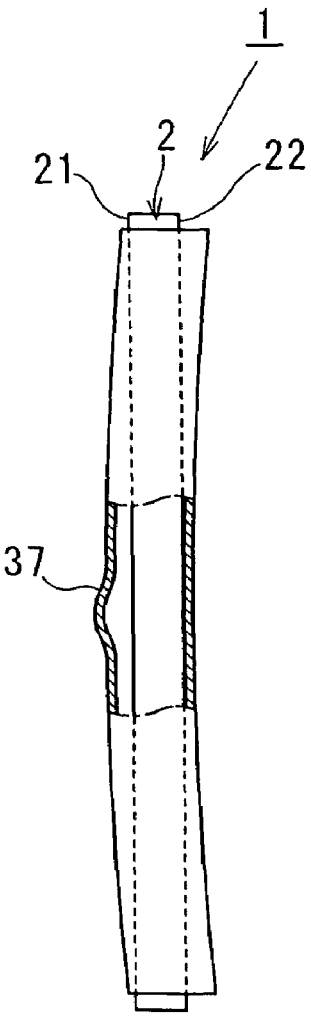
FIG. 16 is a bottom side view of the heat mold device.
Figure 17:
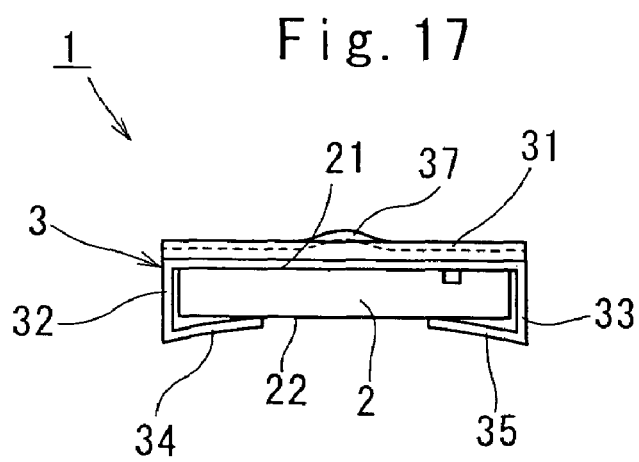
FIG. 17 is an elevational side view of the heat mold device.

FIGS. 15 through 17 show an eighth embodiment of the invention in which a central projection 37 is provided on the lid plate 31 to direct outward, in addition to the lid body 3 being curved along the lengthwise direction.

The projection 37 increases the moment of inertia around the central area of the lid plate 31, thereby making it possible to resist the permanent set in fatigue caused by detachably mounting the lid body 3 against the mold body 2 even under the cyclic environment of the high temperature and the normal temperature.

Ninth Embodiment

Figure 18:
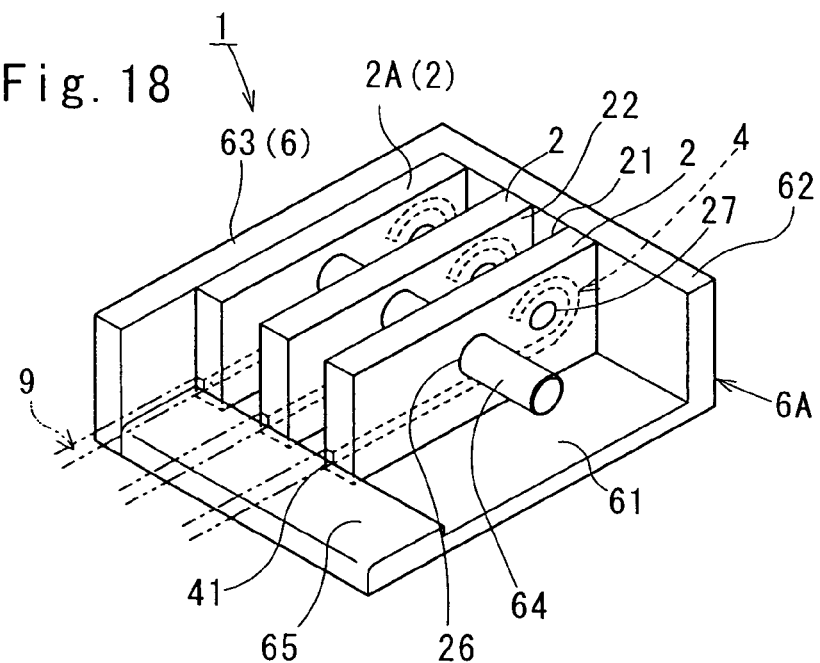
FIG. 18 is a perspective view of a mold frame in which a plurality of heat mold devices are placed according to a ninth embodiment of the invention.
Figure 19:
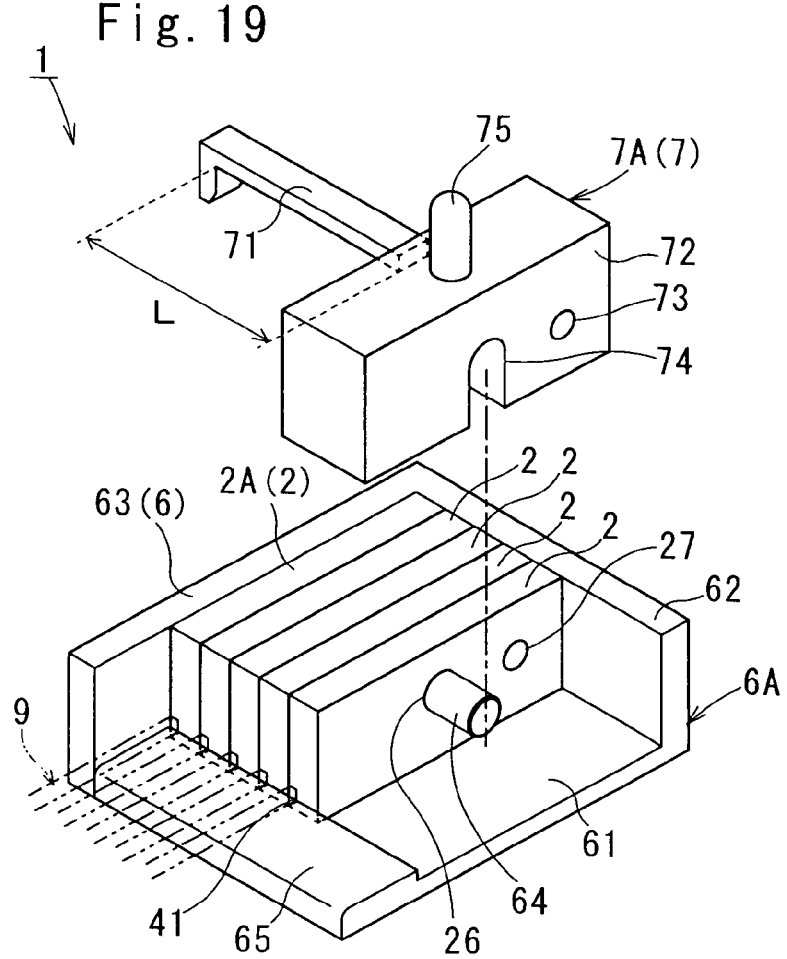
FIG. 19 is a exploded perspective view of the mold frame and a jig arm which serves as a jig member.

FIGS. 18 and 19 show a ninth embodiment of the invention in which the mold body 2 is made from the same sort of material which the metallic coiled wire 91 is formed. A plurality of the metallic mold bodies 2 are contiguously arranged to mutually overlap so as to make the reverse side 22 of one mold body 2 tightly contact with the obverse side 21 of other mold body 2 among the neighboring mold bodies 2. A face plate 6 is provided to engage with the obverse side 21 of the mold body 2 positioned at one end side among the plurality of the mold bodies 2. A securement member 7 is placed to fixedly secure the face plate 6 to the mold body 2.

The array of the mold bodies 2 is placed in a mold frame 6A with the obverse side 21 directed vertical and the lengthwise side laid downward. Each of the mold bodies 2 has a ventilation hole 27 to be surrounded by the arcuate portion of the mold groove 4. A central opening 26 is provided on each of the mold bodies 2 to be pierced through a thickness direction of the mold bodies 2.

The mold frame 6A has a rear wall 62 rising upward from a floor plate 61, and further having a side wall 63 vertically standing on the floor plate 61 in a crosswise relationship with the rear wall 62. The side wall 63 has an elongate pin 64 extending inward in parallel with the floor plate 61. The mold bodies 2 are set in the mold frame 6A with the elongate pin 64 inserted into the central opening 26 as shown in FIG. 18.

In this situation, the mold bodies 2 are placed with the obverse side 21 confronted with the side wall 63 and the open-ended portion 41 located opposite to the rear wall 62.

In this way, the array of the mold bodies 2 are set in the mold frame 6A to tightly engage the reverse side 22 of one mold body 2 with the obverse side 21 of other mold body 2 among the neighboring mold bodies 2 as shown in FIG. 19.

Upon assembling the metallic coiled wires 91 to the mold body 2, the metallic coiled wires 91 remain the respective rest portions outside the mold body 2 through the open-ended portion 41. In order to set the rest portion of the metallic coiled wires 91 in parallel with the open-ended portion 41, a set jig portion 65 is provided as a swollen step plate on an inner side of the floor plate 61. This is to prevent the rest portion of the metallic coiled wires 91 from inadvertently being bent and deformed. This is all the more true because the guide wire 9 is thinned to have a diameter less than 1.0 mm, and liable to deform even under its own weight.

In addition, the rest portion of the metallic coiled wires 91 is susceptible to the convectional heat in the thermal atmosphere and conduction heat transmitted from the mold body 2.

The side wall 63 works herein as the face plate 6 and engages with the obverse side 21 of the leftest mold body 2A to function as the lid body 3 of the first embodiment of the invention. In order to firmly sandwich the array of the mold bodies 2 and the side wall 63, a jig arm 7A is provided as the securement member 7. The jig arm 7A has a hook arm portion 71 and a weight block portion 72 secured to a basal section of the hook arm portion 71. The weight block portion 72 is arranged to be in contact with the reverse side 22 of the rightest mold body 2, and having a ventilation hole 73 in correspondence to the one provided on the mold body 2. The weight block portion 72 further has a grip portion 75 and a notch portion 74 formed to accept the elongate pin 64. A length L of the hook arm portion 71 is equivalent to a total dimension obtained by multiplying a thickness of the single mold body 2 to the number of the mold bodies 2 plus a thickness of the side wall 63.

Upon setting the jig arm 7A to the array of the mold bodies 2, the weight block portion 72 is brought into engagement with the reverse side of the rightest mold body 2, and the hook arm portion 71 hooks the side wall 63 to sandwich the array of the mold bodies 2 and the side wall 63 in unison.

Method of the Ninth Embodiment

The metallic coiled wire 91 is inserted to each of the mold bodies 2 (e.g., five pieces), and the mold bodies 2 are set in the mold frame 6A with the elongate pin 64 inserted in to the central opening 26. Then, the jig arm 7A is placed over the array of the mold bodies 2 set in the mold frame 6A. Thereafter, the mold frame 6A is placed in the furnace with the array of the mold bodies 2 set in the mold frame 6A to thermally treat the metallic coiled wire 91 (shape-forming thermal treatment).

Advantages of the Ninth Embodiment

Such is the structure that the plurality of the mold bodies 2 are contiguously arranged to make the reverse side 22 of one mold body 2 tightly contact with the obverse side 21 of other mold body 2 among the neighboring mold bodies 2. The structure makes it possible to make the one mold body 2 serve as a lid body 3 for the other mold body 2.

The face plate 6 engages with the obverse side 21 of the mold body 2 positioned at one end side among the plurality of the mold bodies 2. This means to eliminate the need of placing the lid body 3 on each of the mold bodies 2 so as to advantageously reduce the number of assembling procedures. With the face plate 6 and the mold bodies 2 snugly fixed by the jig arm 7A, it is possible to prevent the metallic coiled wire 91 from inadvertently falling off the mold body 2.

By arranging the plurality of the mold bodies 2 to mutually overlap, it is possible to dispense with less space in the furnace so as to attain a space-saving advantage, as opposed to the case in which the mold bodies are individually placed in the furnace.

With the length L of the hook arm portion 71 determined to be equivalent to the total dimension obtained by multiplying the thickness of the single mold body 2 to the number of the mold bodies 2 plus a thickness of the side wall 63, it is possible to set the desired number of the mold bodies 2 in the mold frame 6A. It is to be noted that the array of ten mold bodies 2 may be set in the mold frame 6A instead of the five mold bodies 2.

With the jig arm 7A having the length L corresponding to the total thickness of each of the mold bodies 2 and the side plate 63, it is possible to set a predetermined number of the mold bodies 2. By knowing how many metallic coiled wires 91 one unit of the mold body 2 has, it becomes possible to calculate how many guide wires 9 will be produced in total without counting the number of the mold bodies 2 so as to improve the productivity with a high efficiency.

Modification Forms

Figure 20:
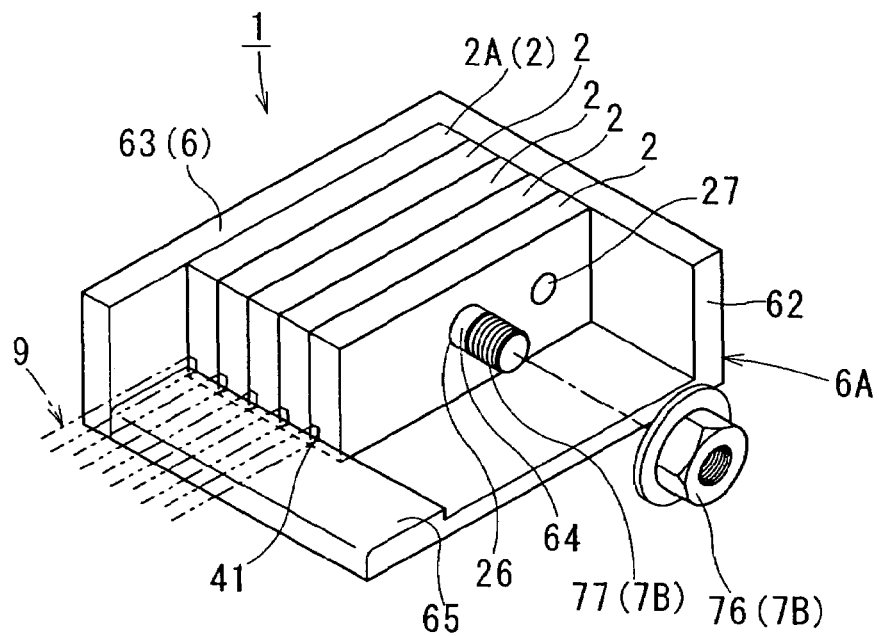
FIG. 20 is a perspective view of the mold frame in which the plurality of the heat mold devices are placed according to a modification form of the ninth embodiment.

FIG. 20 shows a modification form in which a nut-shaped clamp 7B is provided to secure the array of the mold bodies 2 to the side wall 63, instead of the jig arm 7A of the ninth embodiment. The nut-shaped clamp 7B secures its flanged nut 76 to a male-threaded portion 77 of the elongate pin 64.

Figure 21:
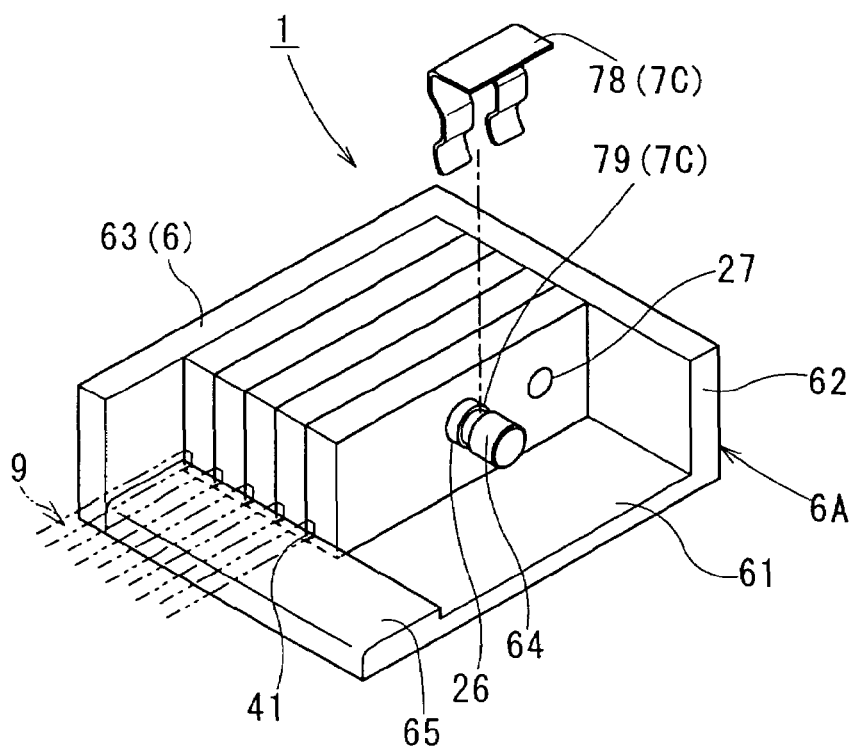
FIG. 21 is a perspective view of the mold frame in which the plurality of the heat mold devices are placed according to another modification form of the ninth embodiment.

FIG. 21 shows another modification form in which an engagement member 7C is provided instead of the jig arm 7A of the ninth embodiment. The engagement member 7C has a leaf clip 78 inserted into a circular groove 79 of the elongate pin 64 to make the clip 78 elastically engage with the reverse side of the rightest mold body 2.

It is to be appreciated that the obverse side of the mold body 2 is used herein in the same meaning as the outer surface 21 of the mold body 2, and the reverse side 22 of the mold body 2 is used in the same meaning as the reverse surface of the mold body 2.

What is claimed is:

1. A heat mold device in which a guide wire formed by a metallic coiled wire has an arcuated portion provided at a predetermined portion of said guide wire by means of a thermal treatment so as to serve as a shape-formed configuration; said heat mold device comprising:

a tabulate metallic mold body, an outer surface of which has a mold groove forming an open-ended portion at an elevational side of said metallic mold body;

a lid body placed on said outer surface of said metallic mold body;

said metallic mold body being made from a material having both thermal expansional coefficient and thermal conductivity which are the same as said metallic coiled wire has; and said lid body having a lid plate to be in contact with said outer surface of said metallic mold body, and further having a pushing member which is slidably fit into said metallic mold body to urgingly push said metallic mold body against said lid plate so as to hold said metallic mold body in place.

2. The heat mold device according to claim 1, wherein said mold groove includes an open-ended portion at both elevational sides of said metallic mold body, and said mold groove extending from said open-ended portion along a path corresponding to said shape-formed configuration.

3. The heat mold device according to claim 1, wherein said mold groove is defined on both the obverse and reverse sides of said metallic mold body.

4. The heat mold device according to claim 1, wherein a plurality of said mold grooves are aligned in parallel with each other.

5. The heat mold device according to claim 1, wherein said pushing member has a side plate extended from both sides of said lid plate in the reverse direction of said metallic mold body, and further having an end plate extended from both the sides of said lid plate to urgingly engage with the reverse side of said metallic mold body.

6. The heat mold device according to claim 5, wherein said pushing member has a protrusion directed toward the obverse side of said metallic mold body.

7. The heat mold, device according to claim 5, wherein said pushing member bends said lid body into a curved configuration with said end plate set inside said lid plate.

8. The heat mold device according to claim 7, wherein said lid plate has a protrusion directed opposite to said end plate.

9. A heat mold device in which a guide wire formed by a metallic coiled wire has an arcuated portion provided at a predetermined portion of said guide wire by means of a thermal treatment so as to serve as a shape-formed configuration; said heat mold device comprising:

a tabulate mold body, an obverse side of which has a mold groove forming an open-ended portion at an elevational side of said metallic mold body;

a lid body placed on said obverse side of said metallic mold body;

said metallic mold body being made from a material having both thermal expansional coefficient and thermal conductivity which are the same as said metallic coiled wire has;

a plurality of said metallic mold bodies being contiguously arranged to mutually overlap so as to make a reverse side of one metallic mold body tightly contact with said obverse side of other metallic mold body among said neighboring metallic mold bodies;

a face plate provided to engage with said obverse side of said metallic mold body positioned at one end side among the plurality of said metallic mold bodies; and a securement member provided to fixedly secure said face plate to said metallic mold body.

10. The heat mold device according to claim 9, wherein said mold groove includes an open-ended portion at both elevational sides of said metallic mold body, and said mold groove extending from said open-ended portion along a path corresponding to said shape-formed configuration.

11. The heat mold device according to claim 9, wherein a plurality of said mold grooves are aligned in parallel with each other.

12. The heat mold device according to claim 9, wherein each of said metallic mold bodies has a ventilation hole.

13. The heat mold device according to claim 9, wherein said securement member has a jig arm to fixedly sandwich said metallic mold body and said face plate together, said jig arm having a predetermined length corresponding to a total thickness of each of said metallic mold bodies and said face plate including a total number of the metallic mold bodies.

* * * * *